United States Patent
Kopperschmidt

(10) Patent No.: US 12,042,585 B2
(45) Date of Patent: Jul. 23, 2024

(54) APPARATUS AND METHOD FOR PREPARING A DIALYSIS SOLUTION

(71) Applicant: Fresenius Medical Care Deutschland GmbH, Bad Homburg (DE)

(72) Inventor: Pascal Kopperschmidt, Dittelbrunn (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 431 days.

(21) Appl. No.: 17/419,574

(22) PCT Filed: Dec. 30, 2019

(86) PCT No.: PCT/EP2019/087163
§ 371 (c)(1),
(2) Date: Jun. 29, 2021

(87) PCT Pub. No.: WO2020/141160
PCT Pub. Date: Jul. 9, 2020

(65) Prior Publication Data
US 2022/0062520 A1    Mar. 3, 2022

(30) Foreign Application Priority Data

Dec. 31, 2018 (DE) ..................... 10 2018 010 174.7

(51) Int. Cl.
*A61M 1/16* (2006.01)

(52) U.S. Cl.
CPC ........ *A61M 1/1668* (2014.02); *A61M 1/1607* (2014.02); *A61M 1/1635* (2014.02); *A61M 2205/3317* (2013.01)

(58) Field of Classification Search
None
See application file for complete search history.

(56) References Cited

U.S. PATENT DOCUMENTS

| | | | |
|---|---|---|---|
| 3,508,656 A | 4/1970 | Serfass et al. | |
| 2018/0333526 A1 | 11/2018 | Sternby | |
| 2022/0143285 A1* | 5/2022 | Hu | A61M 1/1668 |

FOREIGN PATENT DOCUMENTS

| | | |
|---|---|---|
| CA | 1033954 | 7/1978 |
| DE | 2545801 | 4/1976 |

(Continued)

*Primary Examiner* — Richard C Gurtowski
(74) *Attorney, Agent, or Firm* — Jacobson Holman PLLC

(57) ABSTRACT

An apparatus for preparing a dialysis solution has a dialyzate line for conducting a dialysis solution and means configured to discontinuously convey a dialysis solution in the dialyzate line. The apparatus has a conductivity sensor that is arranged to measure the conductivity of the dialysis solution, a concentrate line opening into the dialyzate line upstream of the conductivity sensor at an addition point, a concentrate pump, and a concentrate container from which the concentrate pump conveys concentrate into the concentrate line, and from there, into the dialyzate line. The apparatus has a controller that is connected to the conductivity sensor and to the concentrate pump, and that is configured to control the concentrate pump such that the conductivity fluctuations over time in the dialysis solution downstream of the addition point are reduced with respect to a continuous concentrate conveying.

11 Claims, 1 Drawing Sheet

(56) References Cited

FOREIGN PATENT DOCUMENTS

| EP | 2494998 | 9/2012 |
|----|---------|--------|
| EP | 2962711 | 1/2016 |
| WO | WO 2016/169642 | 10/2016 |

\* cited by examiner

APPARATUS AND METHOD FOR PREPARING A DIALYSIS SOLUTION

BACKGROUND OF THE INVENTION

1. Field of the Invention

The present invention relates to an apparatus for preparing a dialysis solution, wherein the apparatus has a dialyzate line for conducting a dialysis solution and has means that are configured to discontinuously convey a dialysis solution in the dialyzate line, wherein the apparatus has a conductivity sensor that is arranged to measure the conductivity of the dialysis solution, and wherein the apparatus has a concentrate line opening into the dialyzate line upstream of the conductivity sensor at an addition point and having a concentrate pump and has a concentrate container from which the concentrate pump conveys concentrate into the concentrate line and from this into the dialyzate line.

2. Description of Related Art

A dialysis solution is brought into contact with the blood of a patient to be treated indirectly, i.e. separated by a membrane, in a filter or dialyzer to carry out a hemodialysis treatment. In this process, substances are exchanged between the blood and the dialysis solution by diffusion and/or by convection, with contaminants from the blood passing into the dialysis solution over the membrane, whereby the survival of the patient with kidney failure or with a restricted renal function is secured.

It is furthermore known from the prior art to prepare the dialysis solution in that RO water in the hydraulic part of the dialysis machine, i.e. the part of the dialysis machine not acted on by blood, is mixed with an acid concentrate and a base concentrate and in so doing to dilute the concentrates to prepare the ready-to-use dialysis solution.

The correct composition of the dialysis solution is here monitored via conductivity sensors with respect to compatibility with the patient's blood.

The conveying of the fresh dialysis solution to the dialyzer and the drainage of consumed dialysis solution from the dialyzer typically take place by means of a balancing chamber to avoid unwanted volume displacements between the patient and the hydraulic part of the dialysis machine. Known balancing chambers consist of two double chambers that are each divided into two halves by a membrane. While the one half of the double chamber is filled with fresh dialysis solution, a displacement of consumed dialyzate in the other half takes place. The flow paths from and to the double chambers are opened and closed alternately by means of valves. The dialyzate flow is discontinuous due to the alternating filling of the balancing chamber.

This has the disadvantage that the injection of said concentrates into this discontinuous flow can result in conductivity fluctuations or concentration fluctuations at the dialyzer with an insufficient mixture of the components, which is unwanted.

Such a state is shown in FIG. 3. This Figure shows the development of the conductivity at the dialyzer over time and the development of the concentrate injection into the dialyzate line upstream of the dialyzer.

The conductivity fluctuations visible from FIG. 3 are the result of a lack of synchronization of the concentrate supply with the discontinuous volume flow.

It is furthermore known from the prior art to use mixing chambers in said hydraulic circuit to achieve a time-constant conductivity at the dialyzer.

A disadvantage in this procedure, however, comprises the filling volume of the hydraulic circuit being considerably increased by the mixing chambers, which results in extended cleaning cycles in the disinfection of the hydraulic circuit and in longer waiting times in the stabilization of the conductivity after a concentration change during the treatment.

SUMMARY OF THE INVENTION

It is thus the underlying object of the present invention to further develop an apparatus of the initially named kind such that a time-stable conductivity of the dialysis solution at or in the dialyzer is obtained with a comparatively small apparatus effort.

This object is achieved by an apparatus having the features described herein. Provision is accordingly made that the apparatus has a controller or a control or regulation unit that is connected to the conductivity sensor and to the concentrate pump and that the controls the concentrate pump such that the conductivity fluctuations over time in the dialysis solution are reduced with respect to a continuous concentrate conveying.

It is thus the underlying idea of the present invention to control the concentrate supply such that a conductivity of the dialysis solution at or in the dialyzer is achieved that is as constant as possible. The conductivity is measured and a feedback takes place to the concentrate pump in dependence on the measured value such that said concentrate pump is set with regard to its throughput and/or with respect to its operating time and/or operating duration in dependence on the measured conductivity value.

The conductivity measurement thus serves to carry out or modulate the concentrate injection such that a stable, i.e. time-constant or substantially time-constant, conductivity of the dialysis solution supplied to the dialyzer is obtained.

If a regulation takes place, which is likewise covered by the invention, the regulation variable is the conductivity in the dialysis solution supplied to the dialyzer and the control variable is the point in time and/or the time duration and/or the quantity of the supplied concentrate.

The goal is thus the modulation of the concentrate supply or of the concentrate injection such that a time-constant or largely time-constant conductivity of the dialysis solution that is supplied to the dialyzer is obtained.

The controller can be configured in this respect to control the concentrate pump such that the conductivity of this dialysis solution is constant over time or fluctuates in a range from ±1–5% about the mean temporal value of the conductivity.

The apparatus preferably has means for the spectral analysis of the basic pattern of the conductivity modulation with a constant concentrate supply into the dialysis solution, said means being configured to determine the elementary harmonics of the conductivity modulation by spectral analysis.

The controller can be configured here to control the concentrate pump successively for frequencies of the harmonics such that the conductivity is modulated in phase and amplitude such that the associated harmonic contribution is eliminated from the conductivity spectrum.

The controller can be configured to start this procedure with the frequency of the harmonic having the largest amplitude. The frequencies of the next harmonic having the greatest amplitudes are then successively looked for. A modulation of the concentrate supply then takes place such that the contributions in the spectrum of the data determined from the conductivity are eliminated.

Provision can be made alternatively to this that the controller is configured such that it arbitrarily selects the order of the frequencies, that is, for example, the described procedure does not necessarily begin with the frequency of the harmonic having the greatest amplitude.

In an alternative apparatus, the controller is configured to control the concentrate pump in accordance with a trial and error principle. The demonstration of the correct modulation of the concentrate supply is then the large or complete consistency of the conductivity at the dialyzer over time.

The more contributions to the stabilization of the conductivity are required in the discontinuous flow, the greater the magnitude of the successive approximation.

The present invention further relates to a dialysis machine having an apparatus as described herein.

The means that are configured to discontinuously convey a dialysis solution in the dialyzate line are here preferably formed by the balancing chamber(s) of the dialysis machine.

The present invention furthermore relates to a method of preparing a dialysis solution that flows discontinuously through a dialyzate line, wherein a concentrate is supplied to the dialysis solution, and wherein the conductivity of the dialysis solution is measured downstream of the addition point for the concentrate, with the supply of concentrate being controlled such that the conductivity fluctuations over time in the dialysis solution are reduced with respect to a continuous concentrate conveying.

The supply of concentrate can be controlled such that the conductivity of the dialysis solution over time is constant or fluctuates in a range from ±1–5% about the mean time value of the conductivity.

It is conceivable that in a first step with a continuous concentrate supply, the basic pattern of the conductivity modulation is identified and the elementary harmonics of the conductivity modulation are determined by spectral analysis and in a second step, the conductivity is successively modulated in phase and amplitude for frequencies of the harmonics by changing the concentrate supply such that the harmonic contribution is eliminated from the conductivity spectrum.

Said second step can be started at the frequency of the harmonic having the greatest amplitude. It is alternatively possible that the order of the selection of the harmonic is arbitrarily chosen.

It is also possible that the concentrate pump is controlled by the controller in accordance with the trial and error principle to eliminate the conductivity fluctuations over time of the dialysis solution or to reduce them with respect to a concentrate supply such as is shown in FIG. 3.

It is pointed out at this point that the terms "a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

It is also pointed out that the term "dialysis solution" is to be understood broadly and does not only comprise the ready-to-use dialysis solution such as is present in front of the dialyzer, but also an "unfinished" solution in which only one of two or more concentrates are present up to the solvent such as RO water into which the concentrate or concentrates is/are injected or introduced.

BRIEF DESCRIPTION OF THE DRAWINGS

Further details and advantages of the invention will be explained in more detail with reference to an embodiment shown in the drawing.

There are shown:

FIG. 1 shows the desired state of a time-stable, i.e. constant, conductivity of the dialysis solution supplied to the dialyzer.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
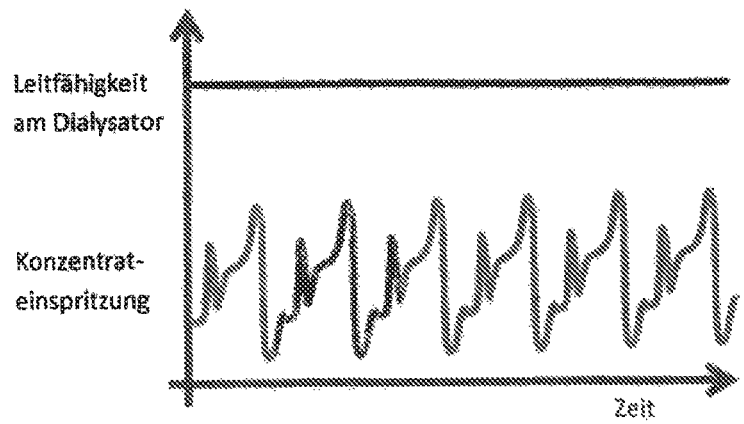
FIG. 1: a regulated, profiled concentrate injection and a stable conductivity, i.e. a conductivity constant over time, that results at the dialyzer.

The progression shown at the bottom in FIG. 1 shows the progression of the concentrate injection over time, with the progression being set such that a constant conductivity results in the dialysis solution that is supplied to the dialyzer despite the discontinuous flow of the dialysis solution, i.e. a flow not constant over time.

Figure 2:
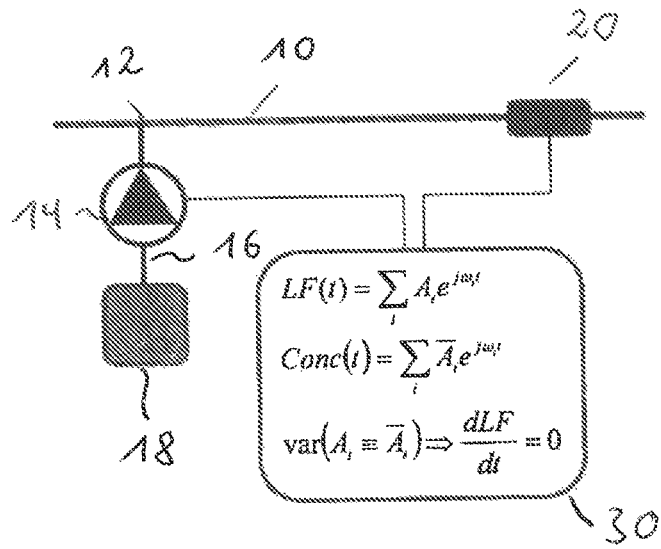
FIG. 2: a scheme for regulating or controlling the concentrate injection or concentrate supply into a discontinuous permeate flow.

To achieve this goal, concentrate from the reservoir 18 is added through the concentrate line 16 by means of the pump 14 into the line 10 leading to the dialyzer (cf. FIG. 2) at the addition point 12 in the direction of flow of the dialysis solution flowing through the line. The measurement of the conductivity takes place by means of the conductivity sensor 20 downstream of this addition point 12.

The signals of said conductivity sensor are supplied to the controller. In a first step with a continuous concentrate injection, the basic pattern of the conductivity modulation is determined and the elementary harmonics of this modulation are determined by spectral analysis.

For example, starting with the frequency of the harmonic having the greatest amplitude, the conductivity is modulated in amplitude and phase by modulation of the concentrate supply in step 2 until the associated harmonic contribution has disappeared from the conductivity spectrum.

The frequencies of the next harmonics having the greatest amplitudes with which the concentrate injection is modulated are successively sought so that the contributions in the spectrum of the data determined from the conductivity have disappeared.

These processes take place in the controller 30 that carries out a corresponding signaling or control of the concentrate pump 14 in dependence on the conductivity values.

Figure 3:
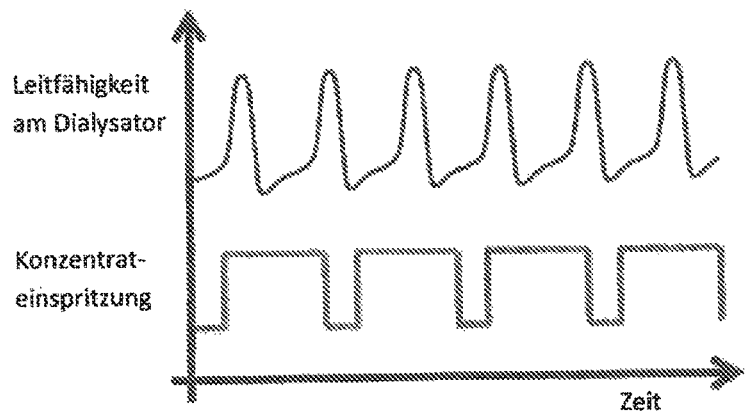
FIG. 3: a non-regulated concentrate injection and an unstable, i.e. time-variable, conductivity at the dialyzer.

It must generally be pointed out that the invention is not restricted to the addition of exactly one concentrate. The injection of a plurality of concentrates is rather also covered by the invention even though only the addition of one concentrate is shown in FIG. 3.

Its addition is modulated in accordance with the invention such that a time-constant or substantially time-constant conductivity and thus a constant concentrate concentration that does not fluctuate over time results in the dialysis solution supplied to the dialyzer.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An apparatus for preparing a dialysis solution, said apparatus comprising:
    a dialyzate line for conducting a dialysis solution, and means that are configured to discontinuously convey a dialysis solution in the dialyzate line, the apparatus having a conductivity sensor that is arranged to measure a conductivity of the dialysis solution, and a concentrate line opening into the dialyzate line upstream of the conductivity sensor at an addition point and having a concentrate pump, and a concentrate container from which the concentrate pump conveys concentrate into the concentrate line, and from the concentrate line into the dialyzate line, a controller that is connected to the conductivity sensor and to the concentrate pump and that is configured to control the concentrate pump such that the conductivity fluctuations over time in the dialysis solution downstream of the addition point are reduced with respect to a continuous concentrate conveying, and
    a means for a spectral analysis of a basic pattern of conductivity modulation with a constant concentrate supply into the dialysis solution, the means being configured to determine the harmonics of the conductivity modulation by spectral analysis, and the controller being configured to successively control the concentrate pump for frequencies of the harmonics such that the conductivity is modulated in phase and amplitude so as to eliminate the harmonic contribution from the conductivity spectrum.

2. The apparatus in accordance with claim 1, wherein the controller is configured to control the concentrate pump such that the conductivity of the dialysis solution over time is constant or fluctuates in a range from ±1–5% about a mean time value of the conductivity.

3. The apparatus in accordance with claim 1, wherein the controller is configured to start at the frequency of the harmonics with the greatest amplitude.

4. The apparatus in accordance with claim 1, wherein the controller is configured such that it arbitrarily selects the order of the frequencies.

5. The apparatus in accordance with claim 1, wherein the controller is configured to control the concentrate pump in accordance with a trial and error principle to minimize conductivity fluctuations of the dialysis solution downstream of the addition point.

6. A dialysis machine having an apparatus in accordance with claim 1.

7. A The dialysis machine in accordance with claim 6, wherein the means are configured to discontinuously convey a dialysis solution in the dialyzate line by which balancing chambers of the dialysis machine are formed.

8. A method of preparing a dialysis solution that flows discontinuously through a dialyzate line, said method comprising:
    supplying a concentrate is to the dialysis solution, and measuring the conductivity of the dialysis solution downstream of the addition point for the concentrate, the supply of concentrate is being controlled such that the conductivity fluctuations over time in the dialysis solution are reduced with respect to a continuous concentrate conveying, and
    in a first step with a continuous concentrate supply, identifying a basic pattern of the conductivity modulation and determining the harmonics of the conductivity modulation by spectral analysis, and in a second step, successively modulating the conductivity in phase and amplitude for frequencies of the harmonics by changing the concentrate supply so as to eliminate the harmonic contribution from the conductivity spectrum.

9. A The method in accordance with claim 8, wherein the supply of concentrate is controlled such that the conductivity of the dialysis solution over time is constant or fluctuates in a range from ±1–5% about a mean time value of the conductivity.

10. A The method in accordance with claim 8, wherein the second step is started at the frequency of the harmonics having the greatest amplitude; or, wherein an order of the selection of the harmonics is arbitrarily selected.

11. A The method in accordance with claim 9, wherein the concentrate pump is controlled in accordance with a trial and error principle to eliminate or reduce the conductivity fluctuations over time of the dialysis solution.

* * * * *